United States Patent
Angeletakis et al.

(10) Patent No.: US 7,625,991 B2
(45) Date of Patent: *Dec. 1, 2009

(54) METHOD FOR MAKING ALKOXY-SILOXANE POLYETHER CARBOXYLATES TERMINATED WITH FUNCTIONAL OLEFIN GROUPS

(75) Inventors: Christos Angeletakis, Orange, CA (US); Matthias Stender, New Milford, CT (US)

(73) Assignee: Kerr Corporation, Orange, CA (US)

( * ) Notice: Subject to any disclaimer, the term of this patent is extended or adjusted under 35 U.S.C. 154(b) by 484 days.

This patent is subject to a terminal disclaimer.

(21) Appl. No.: 11/677,380

(22) Filed: Feb. 21, 2007

(65) Prior Publication Data

US 2007/0197741 A1 Aug. 23, 2007

Related U.S. Application Data

(60) Provisional application No. 60/743,333, filed on Feb. 21, 2006.

(51) Int. Cl.
C08G 77/445 (2006.01)
(52) U.S. Cl. .......................................... 528/29; 528/26
(58) Field of Classification Search .................... 528/26
See application file for complete search history.

(56) References Cited

U.S. PATENT DOCUMENTS

| | | | |
|---|---|---|---|
| 4,584,425 A | 4/1986 | Tom | |
| 4,717,498 A | 1/1988 | Maxon | |
| 4,849,127 A | 7/1989 | Maxon | |
| 5,198,511 A | 3/1993 | Brown-Wensley et al. | |
| 5,266,670 A | 11/1993 | Nakos et al. | |
| 5,296,566 A | 3/1994 | Brown-Wensley et al. | |
| 5,312,881 A | 5/1994 | Marks et al. | |
| 5,330,948 A | 7/1994 | Marks et al. | |
| 5,455,317 A | 10/1995 | Marks et al. | |
| 5,491,206 A | 2/1996 | Brown-Wensley et al. | |
| 5,728,785 A | 3/1998 | Grubbs et al. | |
| 5,831,108 A | 11/1998 | Grubbs et al. | |
| 5,939,504 A | 8/1999 | Woodson, Jr. et al. | |
| 5,942,638 A | 8/1999 | Lichtenhan et al. | |
| 6,001,909 A | 12/1999 | Setiabudi | |
| 6,040,363 A | 3/2000 | Warner et al. | |
| 6,071,459 A | 6/2000 | Warner et al. | |
| 6,075,068 A | 6/2000 | Bissinger | |
| 6,077,805 A | 6/2000 | Van Der Schaaf et al. | |
| 6,121,362 A | 9/2000 | Wanek et al. | |
| 6,252,101 B1 | 6/2001 | Herzig et al. | |
| 6,306,987 B1 | 10/2001 | Van Der Schaaf et al. | |
| 6,310,121 B1 | 10/2001 | Woodson, Jr et al. | |
| 6,323,296 B1 | 11/2001 | Warner et al. | |
| 6,403,522 B1 | 6/2002 | Bolm et al. | |
| 6,407,190 B1 | 6/2002 | Van Der Schaaf et al. | |
| 6,409,875 B1 | 6/2002 | Giardello et al. | |
| 6,410,666 B1 | 6/2002 | Grubbs et al. | |
| 6,417,363 B1 | 7/2002 | Van Der Schaaf et al. | |
| 6,455,029 B1 | 9/2002 | Angeletakis et al. | |
| 6,465,554 B1 | 10/2002 | Van Der Schaaf et al. | |
| 6,521,799 B2 | 2/2003 | Wagener et al. | |
| 6,525,125 B1 | 2/2003 | Giardello et al. | |
| 6,620,955 B1 | 9/2003 | Pederson et al. | |
| 6,649,146 B2 | 11/2003 | Angeletakis et al. | |
| 6,794,534 B2 | 9/2004 | Grubbs et al. | |
| 6,818,586 B2 | 11/2004 | Grubbs et al. | |
| 6,921,735 B2 | 7/2005 | Hoveyda et al. | |
| 7,001,590 B1 | 2/2006 | Angeletakis | |
| 2002/0153096 A1 | 10/2002 | Giardello et al. | |
| 2002/0185630 A1 | 12/2002 | Piccinelli et al. | |
| 2004/0225073 A1 | 11/2004 | Angeletakis | |
| 2005/0159510 A1 | 7/2005 | Smolak et al. | |
| 2006/0173091 A1* | 8/2006 | Angeletakis ................ 523/109 | |

FOREIGN PATENT DOCUMENTS

| | | |
|---|---|---|
| DE | 19859191 A1 | 6/2000 |
| EP | 0771830 A2 | 5/1997 |
| EP | 0796607 A2 | 9/1997 |
| EP | 0940405 A1 | 9/1999 |
| EP | 1025830 A2 | 8/2000 |
| EP | 1241196 A2 | 9/2002 |
| EP | 1317914 A1 | 6/2003 |
| EP | 1555290 A1 | 7/2005 |

(Continued)

OTHER PUBLICATIONS

International Organization for Standardization, Dental elastomeric impression materials; ISO 4823 (1992).

(Continued)

*Primary Examiner*—Randy Gulakowski
*Assistant Examiner*—Lindsay Facteau
(74) *Attorney, Agent, or Firm*—Wood, Herron & Evans, LLP

(57) ABSTRACT

A resin that may be used, for example, in dental impression materials, and a method of making the resin. The resin comprises an alkoxy-siloxane polyester or polyether carboxylate backbone functionalized with at least two cycloolefin groups capable of undergoing a metathesis reaction. The method of making the resin comprises reacting a hydride terminated siloxane with a polyether or polyester diol containing propylene oxide and ethylene oxide fragments, and a cycloolefinic group functionalized hydroxyalkyl carboxylic acid ester, in the presence of a Group 3 or 13 catalyst.

11 Claims, No Drawings

FOREIGN PATENT DOCUMENTS

| | | | |
|---|---|---|---|
| JP | 2001002719 A | 1/2001 | |
| JP | 2002284780 A | 10/2002 | |
| WO | 9839346 A1 | 11/1988 | |
| WO | 9900396 A1 | 1/1999 | |
| WO | 9900397 A1 | 1/1999 | |
| WO | 9929701 A2 | 6/1999 | |
| WO | 9950330 A1 | 10/1999 | |
| WO | 9960030 A1 | 11/1999 | |
| WO | 0046255 A1 | 8/2000 | |
| WO | 0232338 A2 | 4/2002 | |
| WO | 03093351 A1 | 11/2003 | |

OTHER PUBLICATIONS

Scholl et al., Synthesis and activity of a new generation of ruthenium-based olefin metathesis catalysts coordinated with 1,3-dimesityl-4,5-dihydroimidazol-2-ylidene ligands, Org. Lettl, vol. 1, No. 6, 953-956 (1999).

Chevalier et al., Ring-opening olefin metathesis polymerisation (ROMP) as a potential cross-linking mechanism for siloxane polymers, J. of Inorganic and Organometallic Polymers, vol. 9, No. 3, 151-164 (1999).

L. Lecamp et al., Polydimethyl siloxane photoreticulable par vold cationique-I, Eur. Poly. J., vol. 33, No. 9, 1453-1462 (1997).

Kim et al., Surface-initiated ring-opening metathesis polymerization on Si/SiO2, Macromolecules 2000, 33(8), 2793-2795 (2000).

European Patent Office; Search Report and Written Opinion received in corresponding EP Patent Application No. 072507312; dated Sep. 18, 2007; 6 pgs.

* cited by examiner

METHOD FOR MAKING ALKOXY-SILOXANE POLYETHER CARBOXYLATES TERMINATED WITH FUNCTIONAL OLEFIN GROUPS

CROSS REFERENCE TO RELATED APPLICATIONS

Pursuant to 37 C.F.R. § 1.78(a)(4), this application claims the benefit of and priority to prior filed Provisional Application Ser. No. 60/743,333, filed Feb. 21, 2006, which is expressly incorporated herein by reference. This application is related to commonly owned U.S. patent application Ser. No. 11/276,270, filed on Feb. 21, 2006 and entitled POLYETHER-BASED COMPOSITION CURABLE BY METATHESIS REACTION, and to commonly owned U.S. patent application Ser. No. 11/276,273, filed on Feb. 21, 2006 and entitled POLYETHER-BASED DENTAL IMPRESSION MATERIAL CURABLE BY METATHESIS REACTION, which are incorporated herein by reference in their entirety as if completely set forth herein below.

FIELD OF THE INVENTION

This invention relates to a process for making functionalized alkoxy-siloxane polyether carboxylates that are capable of being polymerized by a metathesis reaction.

BACKGROUND OF THE INVENTION

In dentistry, addition silicones are the most widely used impression materials. Addition silicones cure with a hydrosilation mechanism and contain a platinum compound as a catalyst. Despite the addition of various surfactants, the hydrophilicity of the materials as measured by contact angle measurements, especially before set is completed, is very low. This reduces the ability of the impression material to displace oral fluids during curing and results in a compromised impression. Another class of impression material, the polyethers, as exemplified by IMPREGUM® (from 3M ESPE) are 2-part systems containing imine terminated polyether copolymers cured by reaction with a strong acid. However, these polyethers suffer from high rigidity, which is a property of crosslinked polyethers, and poor taste and smell due to the presence of imines and strong acids.

In related U.S. application Ser. Nos. 11/276,270 and 11/276,273 filed on Feb. 21, 2006 and referenced above, compositions containing a resin having a urethane polyester or polyether carboxylate backbone functionalized with at least two cycloolefin groups capable of undergoing a metathesis reaction are described. When used in a dental impression material, however, the composition may be too stiff and brittle, lacking the flexibility of pure addition silicone elastomers. To retain the desired hydrophilicity of a polyether while having the flexibility of an addition silicone, there is a need for a copolymer with both properties that can be used as a resin component together with the urethane polyester or polyether carboxylate.

One category of copolymers having good flexibility is the siloxane polyether (SPE) copolymers. There are many commercially available SPE copolymers. These block copolymers are of two types. One SPE copolymer type is prepared by the hydrosilation reaction of hydride functionalized polydimethylsiloxanes with alkenes. The hydrosilation prepared SPE copolymers contain Si—C—C linkages and can be named alkyl-SPE. There are several commercially available alkyl-SPE copolymers, such as Dow Corning 2-8692 fluid or the Silwet series from GE Silicones. There are many diverse uses for these copolymers, such as nonionic surfactants and defoamers. However the preparation method used for alkyl-SPE, namely hydrosilation, suffers from the disadvantage that it never goes to completion, always resulting in the starting materials being present in the final product, especially the alkene reactant in non-negligible amounts, e.g., at 10% or higher, and other unsaturated impurities. The presence of allyl ethers in the SPE does not generally interfere with many commercial uses of these products, such as for surfactants. But in the case of curing by metathesis reaction, such as ring opening metathesis polymerization (ROMP), the allyl ether impurities do interfere with the metathesis reaction by decreasing the activity of the metal carbene complex catalyst, possibly by irreversible binding. There is therefore a need for a preparation method for an SPE without unsaturated impurities being present in the final product.

Another SPE copolymer type is prepared by a condensation reaction, that is, by the coupling of a chlorine or acetoxy substituted polydimethylsiloxane (PDMS) with an alcohol to afford alkoxy substituted PDMS, but this method suffers from the difficulty of removing the hydrochloric acid or other acid waste and is relatively expensive to scale to large amounts. The condensation prepared SPE copolymers contain Si—O—C linkages and can be named alkoxy-SPE. The alkyl-SPE copolymers are more hydrolytically stable than the alkoxy-SPE in acid conditions. However in neutral or basic conditions their hydrolysis rates are comparable.

The dehydrogenative sylilation of hydride functionalized siloxanes and alcohols is a known synthetic route to highly pure alkoxy functionalized siloxanes (see, e.g., PMSE 2005, 92, 365; PMSE 2004, 91, 587). This dehydrogenation is carried out in the presence of a very strong Lewis acid catalyst, such as tris(pentafluoro-triphenyl)borane, $B(C_6F_5)_3$. This preparatory route is convenient since the byproduct, hydrogen gas, is easy to remove as opposed to the chlorosiloxane route that gives difficult to dispose of hydrochloric acid.

The dehydrogenation of hydride-functionalized polyorganosiloxanes with alcohols has been described in U.S. Patent Application Publication No. US 2004/0186260 ('6260 publication) submitted by Goldschmidt A G. The process disclosed therein is for preparing alkoxy-substituted polyorganosiloxanes using the dehydrogenation reaction in the presence of a main group III and/or transition group III catalyst and optionally a solvent. Specifically, the '6260 publication contains examples relating to the reaction of hydride terminated (alpha, omega disubstituted and/or tethered (comb-like)) polyorganosiloxanes with simple alcohols and simple alcohol started polyethers. However, the '6260 publication does not disclose any specific copolymers or method of making same that provide the desired results in a dental impression material.

There is thus a need for an alkoxy-SPE copolymer with properties that can be used as a resin component together with the urethane polyester or polyether carboxylate for use in a dental impression material, and a process of making the same.

SUMMARY OF THE INVENTION

The invention provides a resin that may be used, for example, in dental impression materials, and a method of making the resin. The resin comprises an alkoxy-siloxane polyester or polyether carboxylate backbone functionalized with at least two cycloolefin groups capable of undergoing a metathesis reaction. The resin has the following formula:

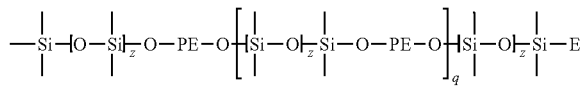

wherein:

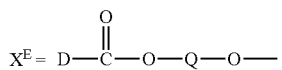

PE is a polyether or polyester fragment,
z=1-500,
q=0-10,
Q is a linear, branched, cyclic or polycyclic organic residue optionally containing siloxane groups (Si—O—Si) and optionally containing heteroatoms selected from the group consisting of B, N, O, Si, P, and S, and D is a cycloolefinic residue and is different than Q.

The method of making the resin comprises reacting a hydride terminated siloxane with a polyether or polyester diol containing propylene oxide and ethylene oxide fragments, and a cycloolefinic group functionalized hydroxyalkyl carboxylic acid ester, in the presence of a Group 3 or 13 catalyst.

DETAILED DESCRIPTION

The present invention provides a resin comprising an alkoxy-siloxane polyether (alkoxy-SPE) carboxylate backbone functionalized with at least two cycloolefin groups capable of undergoing a metathesis reaction. The functional cycloolefin groups may be pendant, terminal or cyclic groups. By "terminal," it is meant that the backbone is terminated at the ends with functional groups. These "terminal groups" may also be referred to herein as "end groups" or "endcappers" and the carboxylate may be referred to as "endcapped." By way of example, the resin may comprise an alkoxy-siloxane polyether norbornenecarboxylate. In one embodiment of the present invention, the resin may be a mixture of a first resin component, namely the alkoxy-SPE carboxylate, and a second resin component, namely a siloxane carboxylate backbone functionalized with cycloolefin groups capable of undergoing a metathesis reaction, which cycloolefin groups may be pendant, terminal or cyclic groups.

In one embodiment, the functional cycloolefin groups in the resin are norbornenyl or norbornenylethyl groups. In another embodiment, the groups are cyclopentenyl, 7-oxanorbornenyl, norbornadienyl, and/or 7-oxanorbornadienyl.

We found that an alkoxy-SPE norbornenecarboxylate (e.g., terminated with norbornenyl groups) prepared by dehydrogenation when added to the resin formulation of a dental impression material containing a urethane polyether (UPE) norbornenecarboxylate afforded the desired properties of increased flexibility and hydrophilicity. This can be explained as being due to the presence of the siloxane segments in the alkoxy-SPE norbornenecarboxylate. In order to decrease the working time, a small amount was added of a pendant siloxane norbornenecarboxylate prepared by dehydrogenation.

Several alkoxy-SPE norbornenecarboxylates were prepared using the dehydrogenation process by reacting a hydride-terminated siloxane with a diol and hydroxypropyl norbornenecarboxylate (HPNBC) as an endcapper. Several siloxane norbornenecarboxylates were also prepared as the simple pendant, terminal and cyclic adducts of HPNBC with the corresponding hydride functional siloxanes, also using the dehydrogenation process.

In accordance with the present invention, the alkoxy-SPE carboxylate has the general formula:

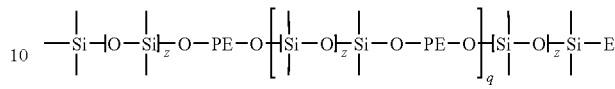

wherein:

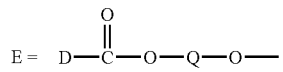

PE is a polyether or polyester fragment,
z=1-500,
q=0-10,
Q is a linear, branched, cyclic or polycyclic organic residue optionally containing siloxane groups (Si—O—Si) and optionally containing heteroatoms selected from the group consisting of B, N, O, Si, P, and S, and D is a cycloolefinic residue and is different than Q. By way of example, D may be a cycloolefinic residue selected from norbornenyl, norbornenylethyl, cyclopentenyl, 7-oxanorbornenyl, norbornadienyl, and/or 7-oxanorbornadienyl.

In one embodiment of the present invention, PE is a polyether containing propylene oxide (PO) and ethylene oxide (EO) fragments, z=1-50, q=0-1 and E=a cycloolefinic endcapper. In a further embodiment, z is about 16 and q is 0 or 1. In another embodiment, the second base resin may be an alkoxy-siloxane polyether norbornenecarboxylate. In a further embodiment, E may have the following structure:

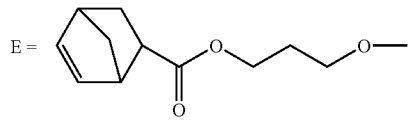

By way of example, the alkoxy-SPE carboxylate may be an encapped alkoxy-siloxane polyether norbornenecarboxylate.

In the embodiment of the present invention in which the resin may be a mixture of a first resin component, namely the alkoxy-SPE carboxylate, and a second resin component, namely a siloxane carboxylate, the siloxane carboxylate is at least one of:

a pendant structure having the following formula:

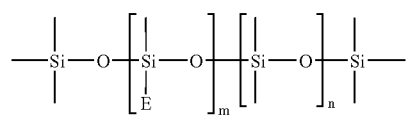

a terminated structure having the following formula:

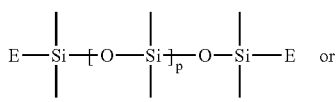 or a cyclic structure having the following formula:

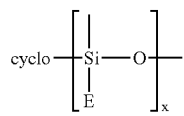

where m=1-50, n=0-200, p=0-200, x=3-6 and E is a cycloolefinic residue. In an exemplary embodiment, the siloxane carboxylate is a pendant structure. In a further exemplary embodiment, m is about 4 and n is about 20. In a further embodiment, E may have the following structure:

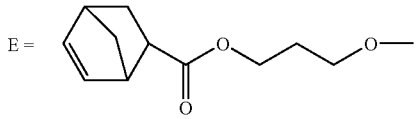

EXAMPLES

Several endcapped alkoxy-SPE norbornenecarboxylates were prepared. The compound E-H is hydroxypropyl norbornenecarboxylate (HPNBC):

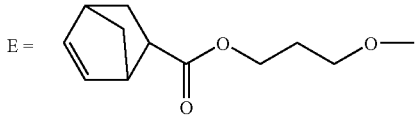

A procedure used for the preparation of alkoxy-SPE norbornenecarboxylates was as follows: 1198.1 g of an EO-PO, EO tipped, polyether diol (Bayer, MULTRANOL® 9111, MW 4000, 800 cps) and 128.9 g of HPNBC were placed in a jacketed 2 L reactor under a nitrogen atmosphere. It was stripped in vacuum at 100° C. for 1 hour with a vacuum below 30 mbar under moderate stirring. Then the temperature was lowered to 90° C. and 0.985 g of the catalyst $B(C_6F_5)_3$ was added under a stream of nitrogen. 673.0 g of a hydrogen-terminated polysiloxane (Gelest, DMS-H11, MW 1000-1100, 7-10 cps, SiH=2.1 mmol/g) were added under vigorous stirring at an addition rate of ca. 10 mL/min. Hydrogen gas evolution was observed through a silicone oil bubbler. It was stirred for another hour and then the Si—H disappearance was monitored by IR. When no more Si—H stretch (ca. 2170 $cm^{-1}$) could be found, the reaction was stopped. When Si—H was still detected, a small amount of HPNBC was added and it was again checked by IR after 1 hour. With respect to the formula provided in the previous paragraph, PE was polyether, z was about 16 and q was 0-1. The theoretical weight average molecular weight was about 6360.

For several analogs, some analytical data such as product viscosity and HPNBC remaining as determined via an HPLC assay are shown in Table 1 below. The Shore A hardness and the work/set time properties when combined with the following catalyst complex (Catalyst 3-1) in a standard test are also shown:

3-1

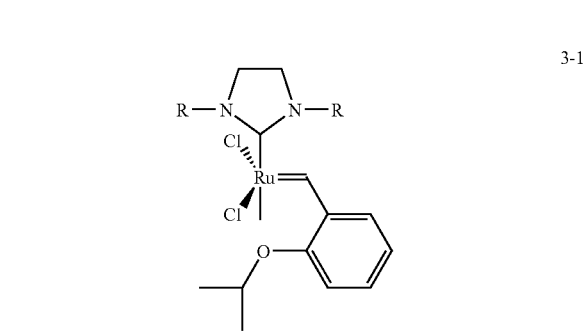

wherein R is mesityl.

TABLE 1

| Compound | MW PDMS | MW PE | Viscosity [cps] | Wt % Residual HPNBC (HPLC) | MW by GPC | Shore A | WT/ST [sec] |
|---|---|---|---|---|---|---|---|
| A1 | 1050 | 4000 | 2440 | 0.7 | 10600, 5900 | 31(1) | 60/100 |
| B1 | 450 | 4000 | 1950 | 3.1 | 10350, 5350 | 19(1) | 75/150 |
| C1 | 6000 | 4000 | 7400 | 3.0 | 15500, 11600, 5200 | 22(1) | 40/90 |
| D1 | 770 | 4000 | 2000 | 1.1 | 10800, 5800 | 25(1) | 80/160 |
| E1 | 133 | 4000 | 1400 | 4.0 | 9400, 4500 | 7(1) | 230/420 |
| F1 | 450 | 4000 | 2850 | 3.0 | 10800, 5900 | 27(1) | 50/95 |
| G1 | 667 | 2000 | 460 | 0.8 | 6100, 3100 | brittle | 29/37 |
| H1 | 770 | 400 | 95 | 2.0 | 2250 | brittle | 19/27 |

Three different types of siloxane norbornenecarboxylates were prepared using HPNBC, pendant, terminated and cyclic as shown in the following schemes:

Pendant

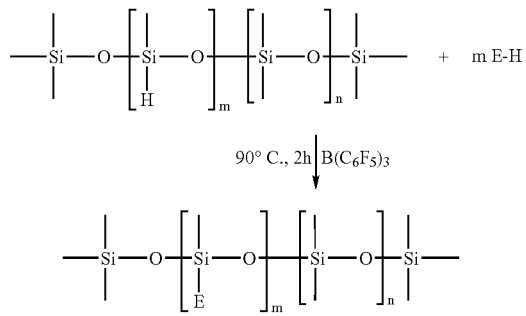

Terminated

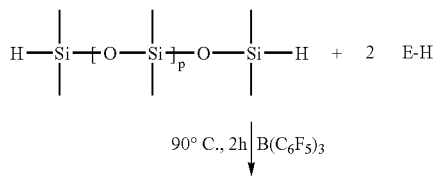

-continued

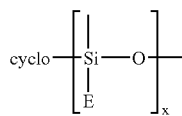

Cyclic

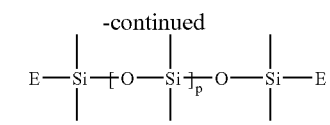

For the above pendant, terminated and cyclic structures, m=1-50, n=0-200, p=0-200, x=3-6.

A procedure used for the preparation of siloxane norbornenecarboxylates was as follows: 329.7 g of HPNBC were placed in a jacketed 2 L reactor under a nitrogen atmosphere. The temperature was raised to 90° C. and 0.819 g of the catalyst $B(C_6F_5)_3$ was added under a stream of nitrogen. 800 g of tethered hydrosiloxane (Gelest, HMS-151, MW 1900-2000, 30 cps, SiH=2.1 mmol/g) were added under vigorous stirring at an addition rate of ca. 10 mL/min. Hydrogen gas evolution was observed through a silicone oil bubbler. It was stirred for another hour and then the Si—H disappearance was monitored by IR. When no more Si—H stretch (ca. 2170 cm$^{-1}$) could be found, the reaction was stopped. When Si—H was still detected, a small amount of HPNBC was added and it was again checked by IR after 1 hour.

Some analytical data such as product viscosity and HPNBC remaining as determined via an HPLC assay are shown in Table 2 below. The shore A hardness and the work/set time properties when combined with catalyst 3-1 in a standard test are also shown.

TABLE 2

| Compound # | Hydrogen siloxane type | Hydrogen siloxane viscosity (csk) | Hydrogen siloxane SiH mmol/g | Product Viscosity (csk) | Wt % HPNBC (HPLC) | Shore A | WT/ST [sec] |
|---|---|---|---|---|---|---|---|
| A2 | pendant | 30 | 1.0 | 230 | 0.5 | hard, crumbly | 9/16 |
| B2 | pendant | 10 | 1.9 | 245 | 24.6 | 74 | 28/55 |
| C2 | pendant | 45 | 4.3 | 880 | 4.4 | 57 | 11/25 |
| D2 | terminated | 2-3 | 4.4 | 30 | 2.2 | 86 | 9/17 |
| E2 | terminated | 0.5 | 15.0 | 33 | 1.6 | crumbled | 13/35 |
| F2 | cyclic |  | 16.6 | 4400 | 5.0 | 78 (Shore D) | 45/130 |
| G2 | cyclic |  | 16.6 | 8800 | 14.8 | no cure | no cure |

From the above, it can be seen that both structural types, alkoxy-SPE norbornene-carboxylates and siloxane norbornenecarboxylates cure when combined with a ruthenium carbene complex catalyst, such as a catalyst having the 3-1 structure.

With respect to the method of making the alkoxy-SPE carboxylates of the present invention, a specific method has been disclosed. However, the invention is not so limited. Broadly, in accordance with the present invention, the method of making cycloolefinic functionalized alkoxy-SPE carboxylates includes reacting a hydride terminated siloxane with (a) a polyether or polyester diol containing propylene oxide and ethylene oxide fragments and (b) a cycloolefinic group functionalized hydroxyalkyl carboxylic acid ester, in the presence of a catalyst. The catalyst may be a Group 3 or 13 (formerly collectively Group III) catalyst. Examples of catalysts are set forth in U.S. Patent Application Publication No. US 2004/

0186260, paragraphs 0021-0029 of which are incorporated by reference herein. An exemplary catalyst is tris(pentafluoro-triphenyl)borane, $B(C_6F_5)_3$.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention is therefore not limited to the specific details, representative apparatus and method and illustrative examples shown and described. Accordingly, departures may be made from such details without departing from the scope of the general inventive concept.

What is claimed is:

1. A resin comprising an alkoxy-siloxane polyester or polyether carboxylate backbone functionalized with at least two cycloolefin groups capable of undergoing a metathesis reaction, and having the formula:

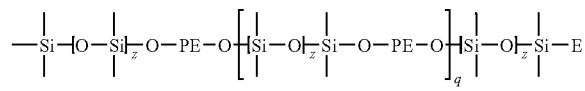

wherein:

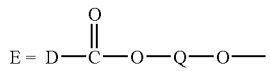

PE is a polyether or polyester fragment,
z=1-500,
q=0-10,
Q is a linear, branched, cyclic or polycyclic organic residue optionally containing siloxane groups (Si-O-Si) and optionally containing heteroatoms selected from the group consisting of B, N, O, Si, P, and S, and
D is a cycloolefinic residue and is different than Q.

2. The resin of claim 1 wherein D is a cycloolefinic residue selected from the group consisting of norbornenyl, norbornenylethyl, cyclopentenyl, 7-oxanorbornenyl, norbornadienyl, and 7-oxanorbornadienyl.

3. The resin of claim 1 wherein PE is a polyether containing propylene oxide (PO) and ethylene oxide (EO) fragments, z is about 16, q=0 or 1 and

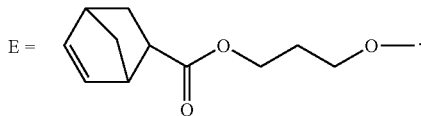

4. The resin of claim 1 wherein PE is a polyether containing propylene oxide (PO) and ethylene oxide (EO) fragments, z=1-50, q=0-1 and

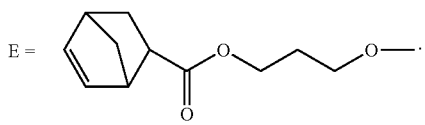

5. The resin of claim 1 further comprising a siloxane carboxylate backbone functionalized with at least two cycloolefin groups capable of undergoing a metathesis reaction, and being at least one of:

a pendant structure having the following formula:

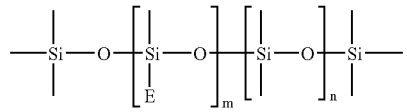

a terminated structure having the following formula:

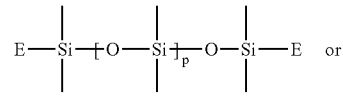 or a cyclic structure having the following formula:

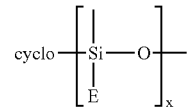

where m 1-50, n=0-200, p=0-200, x=3-6 and E is a cycloolefinic residue.

6. The resin of claim 5 wherein E is a cycloolefinic residue selected from the group consisting of norbornenyl, norbornenylethyl, cyclopentenyl, 7-oxanorbornenyl, norbornadienyl, and 7-oxanorbornadienyl.

7. The resin of claim 6 wherein D is a cycloolefinic residue selected from the group consisting of norbornenyl, norbornenylethyl, cyclopentenyl, 7-oxanorbornenyl, norbornadienyl, and 7-oxanorbornadienyl.

8. The resin of claim 7 wherein PE is a polyether containing propylene oxide (PO) and ethylene oxide (EO) fragments, z=1-50, q=0-1 and

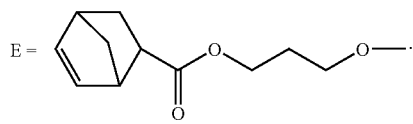

9. A method of making a cycloolefinic functionalized alkoxy-siloxane polyester or polyether carboxylate, comprising reacting a hydride terminated siloxane with:
   (a) a polyether or polyester diol containing propylene oxide and ethylene oxide fragments, and
   (b) a cycloolefinic group functionalized hydroxyalkyl carboxylic acid ester, in the presence of a Group 3 or 13 catalyst.

10. The method of claim 9 wherein the catalyst is tris(pentafluoro-triphenyl)borane.

11. The method of claim 9 wherein (b) is hydroxypropyl norbornenecarboxylate.

* * * * *

UNITED STATES PATENT AND TRADEMARK OFFICE
CERTIFICATE OF CORRECTION

PATENT NO. : 7,625,991 B2  Page 1 of 2
APPLICATION NO. : 11/677380
DATED : December 1, 2009
INVENTOR(S) : Christos Angeletakis and Matthias Stender It is certified that error appears in the above-identified patent and that said Letters Patent is hereby corrected as shown below:

Col. 3, line 4, "  " should read

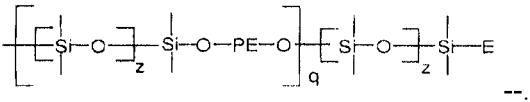 --.

Col. 4, line 10, " 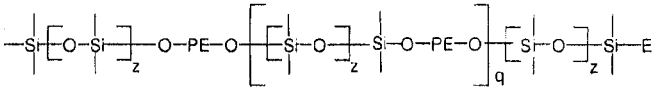 " should read

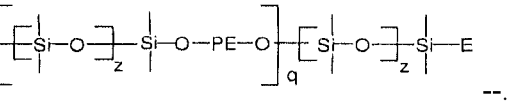 --.

Col. 5, line 38, "E = 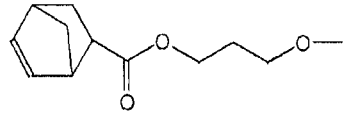 " should read

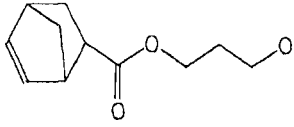 --.

Signed and Sealed this

Twenty-seventh Day of April, 2010

David J. Kappos
*Director of the United States Patent and Trademark Office*

CERTIFICATE OF CORRECTION (continued)
U.S. Pat. No. 7,625,991 B2

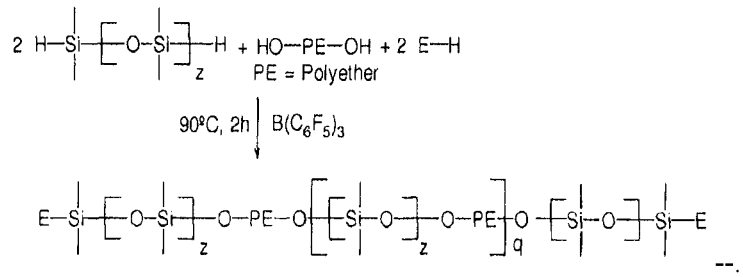

Col. 9, line 20, claim 1, " 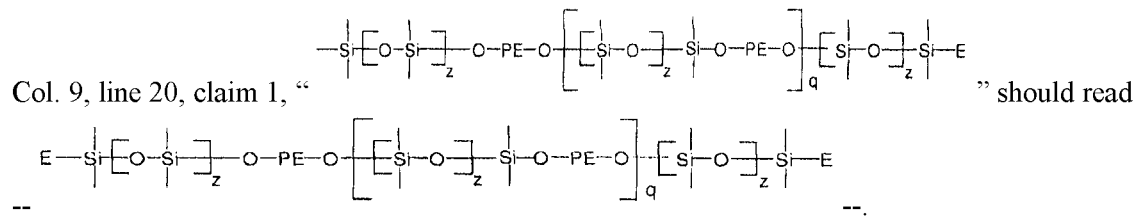 " should read

Col. 10, line 31, claim 5, "where m 1-50" should read --where m=1-50--.